(12) United States Patent
Godec et al.

(10) Patent No.: US 6,183,695 B1
(45) Date of Patent: Feb. 6, 2001

(54) REAGENTLESS OXIDATION REACTOR AND METHODS FOR USING SAME

(75) Inventors: Richard D. Godec, Longmont; Paul P. Kosenka, Denver; Richard S. Hutte, Boulder, all of CO (US)

(73) Assignee: Sievers Instruments, Inc., Boulder, CO (US)

( * ) Notice: Under 35 U.S.C. 154(b), the term of this patent shall be extended for 0 days.

(21) Appl. No.: 09/081,974

(22) Filed: May 11, 1998

Related U.S. Application Data

(63) Continuation-in-part of application No. 08/263,610, filed on Jun. 20, 1994, now Pat. No. 5,750,073, which is a continuation-in-part of application No. 07/869,308, filed on Apr. 16, 1992, now Pat. No. 5,443,991, which is a division of application No. 07/487,720, filed on Mar. 2, 1990, now Pat. No. 5,132,094.

(51) Int. Cl.$^7$ .................................................. G01N 33/00
(52) U.S. Cl. ........................ 422/79; 422/76; 422/77; 422/78; 422/80; 436/145; 436/146; 436/150
(58) Field of Search ........................ 422/22, 24, 76, 422/78, 79, 80, 82.02–82.04; 436/145–146, 150–151, 128–134, 126; 204/129, 412, 413; 210/259, 321.75, 321.84, 748, 758, 759

(56) References Cited

U.S. PATENT DOCUMENTS

| | | | |
|---|---|---|---|
| 3,224,837 | 12/1965 | Moyat | 23/230 |
| 3,958,941 | 5/1976 | Regan | 23/253 |
| 4,209,299 | 6/1980 | Carlson | 23/230 |
| 4,277,438 | 7/1981 | Ejzak | 422/80 |
| 4,293,522 | 10/1981 | Winkler | 422/80 |
| 4,504,373 | 3/1985 | Mani et al. | 204/180 |
| 4,547,273 * | 10/1985 | Ayers | 205/440.51 |
| 4,619,902 | 10/1986 | Bernard | 436/145 |
| 4,626,413 | 12/1986 | Blades et al. | 422/78 |
| 4,666,860 | 5/1987 | Blades et al. | 436/146 |
| 4,863,608 * | 9/1989 | Kawai et al. | 210/638 |
| 5,047,212 | 9/1991 | Blades et al. | 422/82.02 |
| 5,132,094 | 7/1992 | Godec et al. | 422/68.1 |
| 5,275,957 | 1/1994 | Blades et al. | 436/133 |
| 5,443,991 | 8/1995 | Godec et al. | 436/145 |
| 5,750,073 * | 5/1998 | Godec et al. | 422/79 |

OTHER PUBLICATIONS

O. Enea et al, New J. Chem. 12, 853–858, Oct. 1988.*
S. Sato et al. J. Phys. Chem. 1981, 85, 336–341.*
T. Nguyen et al. J. Phys. Chem. 1984, 88, 3386–3388.*
K. Hashimoto et al. J. Phys. Chem. 1984, 88, 4083–4088.*
M. Arai et al. J. Chem. Eng. Japan 1992, 25, 761–762.*

* cited by examiner

*Primary Examiner*—Arlen Soderquist
(74) *Attorney, Agent, or Firm*—David Silverstein; Andover-IP-Law

(57) ABSTRACT

An improved apparatus and method is disclosed utilizing hydrogen absorption in combination with photolysis and/or electrolysis for in situ generation, i.e., without the need for adding chemical oxidizing agents, or enhancement of oxidizing conditions used to promote oxidation of organic compounds to form carbon dioxide, and the use of the same in connection with high-accuracy determination of even extremely low levels of organic and/or inorganic carbon compounds both in flowing aqueous streams and in bulk solutions.

21 Claims, 5 Drawing Sheets

REAGENTLESS OXIDATION REACTOR AND METHODS FOR USING SAME

This application is a continuation-in-part of U.S. application Ser. No. 08/263,610, filed Jun. 20, 1994, now U.S. Pat. No. 5,750,073, which was a continuation-in-part of U.S. application Ser. No. 07/869,308 filed Apr. 16, 1992, now U.S. Pat. No. 5,443,991, which, in turn, was a division of U.S. application Ser. No. 07/487,720, filed Mar. 2, 1990, now U.S. Pat. No. 5,132,094.

FIELD OF THE INVENTION

The present invention principally relates to an improved apparatus and method for in situ generation, i.e., without the need for adding chemical oxidizing agents, or enhancement of oxidizing conditions used to promote oxidation of organic compounds to form carbon dioxide, and the use of the same in connection with high-accuracy determination of even extremely low levels of organic and/or inorganic carbon compounds both in flowing aqueous streams and in bulk solutions. This invention has particular utility in determining and monitoring carbon levels in ultrapure water intended for such highly impurity-sensitive applications as in the manufacture of semiconductors. This invention also has utility in such other applications as monitoring various stages of water purification systems and municipal drinking waters.

BACKGROUND OF THE INVENTION

The measurement of the total organic carbon (TOC) concentration, total inorganic carbon (TIC) concentration, and total carbon (TC) concentration in water has become a standard method for ascertaining the level of contamination by organic and inorganic carbon compounds in potable waters, industrial process waters, and municipal and industrial waste waters. In addition to widespread terrestrial applications, the measurement of TOC is one of the primary means for determining the purity of potable and process waters for manned space based systems including the space shuttle, the proposed space station and for future manned explorations of the moon and other planets.

A variety of prior art approaches for measuring the total organic carbon content of water have been proposed, for example, in U.S. Pat. No. 3,958,941 (Regan); U.S. Pat. No. 3,224,837 (Moyat); U.S. Pat. No. 4,293,522 (Winkler); U.S. Pat. No. 4,277,438 (Ejzak); U.S. Pat. Nos. 4,626,413 and 4,666,860 (Blades et al.); U.S. Pat. No. 4,619,902 (Bernard); U.S. Pat. No. 5,275,957 (Blades et al.); and U.S. Pat. Nos. 5,132,094 and 5,443,991 (Godec et al.), each of which is incorporated herein by reference.

Representative of the devices described in these references are the methods described in U.S. Pat. No. 3,958,941 (Regan). In Regan an aqueous sample is introduced into a circulating water stream that flows through a reaction chamber where the sample is mixed with air and exposed to ultraviolet (U.V.) radiation to promote the oxidation of organic compounds to form carbon dioxide. The carbon dioxide formed in the reaction chamber is then removed from solution by an air stripping system and introduced into a second chamber containing water that has been purified to remove ionic compounds. The conductivity of the water in the second chamber is measured, and any increase in conductivity is related to the concentration of carbon dioxide formed in the first reactor. The conduction measurement can be used, therefore, to determine the concentration of organic compounds in the original sample.

But, the Regan device is slow, cannot be used for the continuous monitoring of TOC concentration in flowing aqueous streams, cannot be scaled down without increasing interference from commonly-occurring contaminants, such as $NO_2$, $SO_2$ and $H_2S$, to unacceptable levels, and is therefore generally unsatisfactory. In addition, Regan does not disclose that an aqueous solution of acid must be added to the sample stream to reduce the pH to a value of less than about 4 to insure a reasonable removal rate of carbon dioxide using the air stripping system described. The oxidation method disclosed by Regan is unsatisfactory for the measurement of refractory compounds, particularly urea. In Regan, an aqueous sample of 20 to 100 mL containing 0.5 mg/L organic carbon is required to generate sufficient carbon dioxide for accurate detection, thus limiting the utility of the device for the measurement of sub-part per million levels of TOC in smaller sample sizes. Finally, in practice, the Regan system requires frequent recalibration-typically once per day—due to variations in background conductivity. Also, the concentration of total organic carbon in the calibration standard must be approximately equal to the concentration of organic carbon in the sample. Because of this, recalibration is required when analyzing aqueous samples containing higher or lower levels of organic carbon when compared with the calibration standard.

Another method and apparatus for the measurement of organic content of aqueous samples is that described in U.S. Pat. No. 4,277,438 (Ejzak). Ejzak describes a multistage reactor design which provides for the addition of oxygen and a chemical oxidizing agent, preferably sodium persulfate, to the aqueous sample stream prior to oxidation of the stream using ultraviolet radiation in a series of reactors. Ejzak also describes the use of an inorganic carbon stripping process—before oxidation of the organic carbon—that includes the addition of phosphoric acid to the sample stream. After oxidation, the sample stream is passed into a gas-liquid separator where the added oxygen acts as a carrier gas to strip carbon dioxide and other gases from the aqueous solution. In the preferred embodiment, the gas stream is then passed through an acid mist eliminator, a coalescer and salt collector, and through a particle filter prior to passage into an infrared (IR) detector for the measurement of the concentration or carbon dioxide in the gas stream.

The methods and apparatus disclosed by Ejzak provide certain improvements over the Regan patent; however, the Ejzak device requires extensive manual operation and is generally unsatisfactory for other reasons as well. Thus, the Ejzak device requires three external chemical reagents: oxygen gas, aqueous phosphoric acid and an aqueous solution of sodium persulfate. Both the phosphoric acid and persulfate solutions must be prepared at frequent intervals by the operator due to the relatively high rate of consumption. The Ejzak device requires dilution of the sample if the solution contains high concentrations of salts in order to insure complete oxidation of the sample and to eliminate fouling of the particle filter located prior to the IR carbon dioxide detector. As in the Regan patent, relatively large sample sizes are required—typically 20 mL of sample for accurate measurement at 0.5 mg/L total organic carbon—and the carbon dioxide formed in the oxidation chamber is removed using a gravity dependent technique that cannot be easily used in space-based operations.

Still another method and apparatus for the measurement of total organic carbon in water is disclosed in U.S. Pat. No. 4,293,522 (Winkler). In Winkler, an oxidizing agent, specifically molecular oxygen, is generated in situ by the electrolysis of water. Organic compounds are subsequently oxidized to form carbon dioxide by a combination of exposure to U.V. radiation and the in situ-generated oxygen.

Winkler does not teach or suggest, however, that the aqueous sample stream be acidified to assist in the removal of carbon dioxide from solution. On the contrary, Winkler teaches away from the use of acid. Therefore, the Winkler method and apparatus cannot be used for high accuracy measurement of very low levels of organic compounds in basic aqueous samples. Also, the oxidation chamber of Winkler uses a solid electrolyte to separate the two electrodes employed for the electrolysis of water. The solid electrolyte described by Winkler is composed of an organic polymer which, under exposure to oxygen, ozone and U.V. radiation, will undergo oxidation to form carbon dioxide, therefore resulting in unacceptable and misleading background levels of carbon and/or organic compounds in the sample stream. These background levels of carbon and/or organic compounds, though typically small, become proportionally very large and increasingly significant sources of error at very low organic compound concentrations in the sample.

Winkler also describes a conductometric carbon dioxide detection system wherein the sample stream exiting the oxidizing chamber must be held in an equilibriating relationship to a stream of deionized water. The two flowing streams are separated by a $CO_2$ permeable membrane that allows the concentration of carbon dioxide to equilibrate between the streams. The concentration of carbon dioxide is then determined by measuring the conductance of the deionized water stream which has absorbed $CO_2$ which has diffused through the membrane. However, the use of two flowing streams introduces operating parameters into the detection process resulting in the need for frequent calibration adjustments.

Another example of the prior art in this field is U.S. Pat. No. 4,619,902 (Bernard), which teaches the oxidation of organic compounds to form carbon dioxide using persulfate oxidation at elevated temperatures—typically 20° to 100° C.—in the presence of a platinum metal catalyst. Bernard recognizes that the materials used in the construction of instrumentation for the determination of total organic carbon in water can contribute organic compounds to the sample during the measurement process, and teaches that inert materials, such as polytetrafluoroethylene (PTFE), must be used to minimize this background interference. As with the previously mentioned patent, a gas stripping technique is employed to collect the formed carbon dioxide, and measurement is made using IR spectrometry. Bernard also recognizes that aqueous solutions of sodium persulfate are not stable due to auto-degradation of the reagent, thus requiring fresh supplies.

Another system for the measurement of organic compounds in deionized water is described in U.S. Pat. No. 4,626,413 (Blades and Godec). The apparatus described by Blades and Godec is based on direct U.V. oxidation of organic compounds to form carbon dioxide, which is then measured by using conductometric detection. In the Blades and Godec patent, the oxidation of some organic compounds results in the formation of strong acids, such as HCl, $H_2SO_4$ and HNO3, which then interfere with the conductometric measurements. The Blades and Godec patent is also limited to the measurement of total organic compounds in deionized water and cannot be used for samples containing ionic compounds other than bicarbonate ion. Additionally, the levels of TOC detection are limited by the availability of dissolved oxygen in the sample and the small amounts of hydroxyl radicals generated from the photolysis of water from 185 nm radiation.

U.S. Pat. No. 4,626,413 (Blades and Godec) is also the parent of a series of subsequent patents, each based at least in part, on the parent case, but also adding additional disclosure and refinements of various types. Included in this series of subsequent related patents are U.S. Pat. Nos. 4,666,860; 5,047,212; and 5,275,957. The latter patent suggests, for example, that electrophoresis can be used to speed the reaction, but it fails to teach the types of electrolytic oxidation cells which are the subject of this invention.

In U.S. Pat. No. 4,209,299 (Carlson), it is disclosed that the concentration of volatile materials in a liquid can be quantitatively determined by transferring the desired material through a gas permeable membrane into a liquid of known conductivity, such as deionized water. The Carlson device is demonstrated for the measurement of a number of volatile organic and inorganic compounds, but Carlson does not suggest the combination of this process in conjunction with a carbon dioxide producing reactor.

The use of aqueous solutions of persulfate salts for the oxidation of organic compounds is widely known. For example, Smit and Hoogland (16 Electrochima Acta, 1–18 (1971)) demonstrate that persulfate ions and other oxidizing agents can be electrochemically generated. Also, U.S. Pat. No. 4,504,373 (Mani et. al.), describes a method for the electrochemical generation of acid and base from aqueous salt solutions.

In electrochemical reactions in aqueous solutions, a common reduction product is hydrogen gas. Because of its flammability, the hydrogen presents a potential hazard in devices using electrochemical techniques. The interaction of hydrogen gas in aqueous solutions and palladium metal is well known (e.g., F. A. Lewis, "The Palladium Hydrogen System," Academic Press, 1967, London, incorporated herein by this reference); and, the use of palladium offers a potential solution to the generation of hydrogen in electrochemical reactions by selective removal and disposal of the hydrogen.

The foregoing prior art processes and apparatus, however, have been unable to meet the increasingly demanding industry standards for ultrapure water, for example in pharmaceuticals, semiconductors and other such applications. Accurate measurement of carbon (as TOC or total organic carbon) in the 50–1000 parts per billion range, for example, is required to support new developments in semiconductor manufacturing. But, the prior art technology cannot accurately measure TOC in ultrapure water, which typically has a very low level of dissolved oxygen that is insufficient to oxidize all of the organic compounds in a sample to carbon dioxide. The result is an inaccurate and misleadingly low reading which suggests the water sample is purer than in fact is the case. This problem is exacerbated when the water sample contains an excess of residual hydrogen gas (e.g., 40 to 100 ppb $H_2$), as might be found in one of the catalytic removal unit processes in semiconductor manufacture. In these cases, carbon measurements made using prior art technology may reflect as little as 18% to 22% of the correct value.

Adding sufficient oxygen to the water sample either before or during the analysis without also adding contaminants and creating other process problems, however, is not easy to accomplish. Thus, it is extremely difficult to diffuse enough additional oxygen obtained from air, or to just diffuse in ambient air, into the water sample without also introducing organic materials and/or atmospheric carbon dioxide, either of which would lead in inaccurate carbon measurements. In these cases, the carbon readings would suggest that the water sample was less pure than in fact is the case. Similarly, the addition of non-gaseous chemical oxidizing agents to a water sample raises possible problems of organic contaminants or introduces other process difficulties. Electrolysis of the ultrapure water in the sample itself could be a solution, but only as long as it can be done without any addition of extra organic compounds or carbon dioxide to the sample.

APPLICANTS' PRIOR RELATED INVENTIONS

In applicants' related U.S. Pat. Nos. 5,132,094 and 5,443,991, which are incorporated herein by reference, many of the above-described prior art limitations are overcome. Those patents disclose apparatus and method using a selective carbon dioxide-permeable membrane for the transport of carbon dioxide from either an oxidized or unoxidized sample stream into a second aqueous solution where the sensitive detection of carbon dioxide is accomplished using conductometric measurement, thus eliminating the use of a gas stripping apparatus. Those patents also may employ in situ generation of oxidizing conditions, in addition to or in place of utilizing oxidizing agents such as persulfate ions, hydrogen peroxide and molecular oxygen, thus eliminating the need for the introduction of gases and unstable chemical reagents. Also described in applicants' related '094 and '991 patents are invention embodiments wherein an in-line acidification module permits accurate determination of the organic content of aqueous samples over a wide sample pH range, and the incorporation of an oxidation catalyst helps to insure rapid and complete photo-oxidation of organic compounds.

The most recent patent application in this line of applicants' prior related applications, U.S. Ser. No. 08/263,610, now U.S. Pat. No. 5,750,073, which is also incorporated herein by reference, describes apparatus and process in which an aqueous sample stream is passed through a filter to remove any particulate matter, then passed into an acidification module for the introduction of a suitable concentration of acid to cause a reduction in the pH of the solution to a pH of less than 4. Inorganic carbon species—primarily carbonate and bicarbonate ions—are reacted with the acid to form carbon dioxide, while organic compounds remain unreacted. The effluent of the acidification module is directed into an inorganic carbon removal module comprised of either a carbon dioxide selective gas permeable membrane or a non-selective gas permeable membrane, which separates the acidified sample stream from a second aqueous stream in which the pH of the stream has been raised to a pH of greater than 10 by addition of a suitable base. The carbon dioxide formed from the reaction of inorganic carbon species with the acid selectively diffuses across the gas permeable membrane into the basic aqueous stream where the carbon dioxide is converted to ionic species (carbonate or bicarbonate) for subsequent disposal.

The acidic and basic streams used in the acidification module and inorganic carbon removal modules may comprise aqueous solutions of suitable acids and bases or, alternatively, an aqueous salt solution can be passed through a system incorporating a bi-polar membrane (for example, as described in U.S. Pat. No. 4,504,373, which is incorporated herein by reference) for the in situ generation of an acidic stream, a basic stream, and a depleted salt stream.

The effluent of the inorganic carbon removal module (or an aqueous sample either known to be free from inorganic carbon, or one previously treated in some other way to remove or at least measure inorganic carbon) is then directed into an ultraviolet (U.V.) oxidation module or reactor which incorporates direct U.V. oxidation using short wavelength U.V. radiation and U.V. oxidation in the presence of oxidizing conditions generated in situ by the electrolysis of water. In the U.V. oxidation reactor, organic compounds are converted to carbon dioxide. A cathode system selected from the group comprising the so-called "transition" metals (groups III B, IV B, V B, VI B, VII B, VIII, and I B of the periodic table of elements) and alloys thereof, preferably palladium and palladium alloys, particularly a Pd/Ag alloy, platinum and platinum alloys, titanium and titanium alloys, and nickel and nickel alloys, can be employed in the electrolysis apparatus to remove the hydrogen generated during the electrolysis of water thereby producing a net increase of oxygen in the electrolysis cell.

The preferred embodiment of this earlier related application utilized a three electrode system (FIG. 2): electrode #1 (16) was an optically transparent wire screen anode of the primary oxidation electrolysis chamber; electrode #2 (20) was a Pd/Ag (or comparable metallic) alloy bielectrode (connected to ground); and electrode #3 (24) was a stainless steel cathode in the secondary electrolysis chamber. In the primary oxidation electrolysis chamber, oxidation of the organic compounds (and production of oxygen from water) occurred at and near the wire electrode #1 from the net increase of electrochemically generated oxygen in the presence of intense short wave ultraviolet light. Electrochemical reduction of water to form hydrogen occurred at the metallic alloy electrode #2. On the back side of electrode #2, the electrochemical oxidation of water produced oxygen, while electrochemical reduction of water to produce hydrogen occurred at electrode #3. Since the metallic electrode was selected so as to be permeable to hydrogen, the goal was to have hydrogen produced in the primary oxidation reactor diffuse through the metallic electrode. At the metal/solution interface of the secondary electrolysis cell, the hydrogen atoms encounter oxygen, formed from electrolysis of water, and are effectively removed at this interface from the system. The concentration of hydrogen is thereby maintained very close to zero in the secondary electrolysis chamber at electrode #2 to insure a high gradient across the interface.

The carbon dioxide formed in the photoreactor is then sensitively measured using a carbon dioxide sensor. The sensor is comprised of a carbon dioxide selective gas permeable membrane which separates the acidified sample stream from a deionized water reservoir. The deionized water is continuously generated by means of a mixed bed ion exchange resin. Alternatively, deionized water can be supplied from a source external to the apparatus.

In the basic measurement cycle, a first portion or pulse of fresh deionized water is introduced into the deionized water side of the gas permeable membrane and a shut-off valve actuated to stop the flow of deionized water. The effluent of the photoreactor continuously flows on the opposite side of the membrane. The carbon dioxide formed in the photoreactor from the oxidation of organic compounds diffuses across the gas permeable membrane until the concentration of carbon dioxide in the two aqueous streams is substantially the same. As the carbon dioxide enters the deionized water, the carbon dioxide dissolves in the water and causes an increase in the conductivity of the aqueous solution. After equilibrium has been established (typically about 5 min.), a second portion or pulse of fresh deionized water is used to sweep the first equilibrated portion into a conductivity cell in order to measure the increase in the concentration of ionic species in the first portion. The increase in conductivity observed in the deionized water can then be directly related to the concentration of carbon dioxide in the sample stream and hence to the level of organic compounds originally present in the sample stream.

The present application is principally directed to an improved and simplified embodiment of the above-described invention for establishing in situ oxidizing conditions for promoting the oxidation of organic compounds to carbon dioxide as part of a system for highly accurate measurement of even very low levels of concentrations of organic materials in aqueous samples.

OBJECTS OF THE INVENTION

A general object of this invention is, therefore, to provide improved apparatus and methods for oxidizing organic compounds in aqueous samples to carbon dioxide, and for thereafter measuring that carbon dioxide as an indication of the carbon content of the samples.

A principal object of this invention is to provide apparatus and methods for in situ generation of oxidizing conditions in an aqueous sample to promote the oxidation of organic compounds to carbon dioxide, without the need for addition of chemical oxidizing agents.

Another object of this invention is to provide apparatus and methods for absorbing or otherwise removing hydrogen from at least a portion of an aqueous sample so as to aid in creating or enhancing oxidizing conditions in the aqueous sample for promoting the oxidation of organic compounds.

A specific object of this invention is to provide apparatus and methods wherein an aqueous sample containing organic compounds is brought into contact with a suitable metal, metallic alloy, or comparable inorganic hydrogen-absorbing surface, whereby hydrogen is absorbed from the aqueous sample onto the surface of, or is diffused into or through, the metal, alloy or other hydrogen-absorbing material.

It is also a specific object of this invention to provide apparatus and methods wherein an aqueous sample is subjected to one or a combination of conditions under which hydrogen and oxygen components are split from water in the aqueous sample, and hydrogen is at least partially removed from the aqueous sample by absorption onto or diffusion into an inorganic hydrogen-absorbing member, thereby creating an oxygen-enriched environment in the aqueous sample for assisting in the oxidation of organic compounds in the sample to carbon dioxide.

It is still another specific object of this invention to provide apparatus and methods wherein an aqueous sample is subjected to one or a combination of energy inputs, which may include ultraviolet (U.V.) photolysis alone, or electrolysis alone, together with contacting the sample with an inorganic hydrogen-absorbing surface, in order to split hydrogen from water in the sample and remove it, to leave an oxygen-enhanced aqueous sample.

A particular object of this invention is to provide apparatus and methods wherein a combination of U.V. photolysis and electro-oxidation provide substantially complete oxidation of organic compounds in an aqueous sample.

Still another object of this invention is to provide apparatus and methods wherein a hydrogen absorption cycle, during which an aqueous sample is contacted with a suitable inorganic hydrogen-absorbing metal, metallic alloy, or comparable material, and hydrogen is absorbed from the sample onto the metal, alloy or other material, is alternated with a hydrogen desorption, surface-regeneration cycle, during which the surface of the material is flushed with a cleansing fluid, so as to cleanse or purge absorbed hydrogen from the metal, alloy, or other material and thereby restore and recondition the material surface for another hydrogen absorption cycle.

Yet another object of this invention is to provide apparatus and methods wherein electrical fields, in particular electrolysis, are utilized to facilitate the hydrogen absorption cycles, the hydrogen desorption cycles, or both, and which may be used in conjunction with, or without, fluid flushing of the absorption surface during a hydrogen desorption/regeneration cycle.

Other objects and advantages of the present invention will in part be obvious and will in part appear hereinafter. The invention accordingly comprises, but is not limited to, the process and related apparatus, involving the several steps and the various components, and the relation and order of one or more such steps and components with respect to each of the others, as exemplified by the following description and the accompanying drawings. Various modifications of and variations on the process and apparatus as herein described will be apparent to those skilled in the art, and all such modifications and variations are considered within the scope of the invention.

SUMMARY OF THE INVENTION

The essence of this invention, both the original and the simplified versions, is the enhancement of oxidizing conditions in an aqueous sample by at least the partial removal of hydrogen from the sample environment. In some instances, hydrogen is found already dissolved in the original aqueous sample, thereby reducing the oxidation potential based, for example, on any dissolved oxygen in the sample. Hydrogen may also be produced from the splitting of water into hydrogen and oxygen components under conditions of U.V. photolysis, electrolysis or both. Additional hydrogen may be liberated as organic compounds in the sample are oxidized. In all of these cases, removal of hydrogen from the sample environment in accordance with this invention has been found to enhance oxidation efficiency and to enable substantially complete oxidation of organic compounds in the aqueous sample without the addition of chemical oxidizing agents. As used in this application, the term "in situ generation of oxidizing conditions" means either establishing or enhancing the oxidizing conditions in an aqueous sample to promote oxidation of organic compounds without addition of chemical oxidizing agents, oxygen or ozone.

In a first embodiment of this simplified practice of the underlying carbon detection invention, an enhanced oxidizing environment for oxidizing organic carbon compounds in an aqueous sample to carbon dioxide is provided in situ at least in part by the splitting of water in the aqueous sample into hydrogen and oxygen components under action of photolysis or other mode of energy supply, together with the absorption or other process for the removal of hydrogen, onto a surface of, or into the body of, an inorganic hydrogen-absorbing member, thereby establishing an oxygen-enriched environment in at least a portion of the aqueous sample. In a second embodiment of the simplified invention practice, the inorganic hydrogen-absorbing member is also electrically conductive. An electric field-facilitated, in particular electrolysis-facilitated, hydrogen absorption period is typically followed by an electric field or electrolysis-facilitated periodic desorption of hydrogen from the electrically-conductive, hydrogen-absorbing member during a cleansing/regeneration/desorption cycle. In this second embodiment, an electric field or potential established between the hydrogen-absorbing electrode member and a second electrode member is used to promote the splitting of water and/or absorption of hydrogen during an absorption cycle. Reversing electrical polarity between these two electrodes can then be used to facilitate desorption of hydrogen from the hydrogen-absorbing electrode during a cleansing/regeneration/desorption cycle.

Depending on the choice of the hydrogen-absorbing electrode and the amount of oxygen enrichment or oxidation potential required for substantially complete oxidation of organic compounds in a sample, varying in accordance with the amounts of organic compounds in the aqueous sample and the level of dissolved oxygen, in a third variant of the present invention, an electrical potential may also be established between the hydrogen-absorbing electrode and a third electrode separated from the hydrogen-absorbing electrode by an ionic (electrically-conductive) liquid medium. This further electrolysis embodiment of the invention can be utilized either in conjunction with cyclical hydrogen absorption/desorption cycles, as described above; or, alternatively, as described in connection with an earlier embodiment of the invention (application Ser. No. 08/263,610 now U.S. Pat. No. 5,750,073), at least a portion of the hydrogen removed from the aqueous sample can be diffused through to the opposite side of the hydrogen-absorbing electrode and removed therefrom, for example, by recombination with oxygen in a second aqueous medium.

In an embodiment of this invention particularly useful for aqueous samples having relatively higher levels of organic compounds, some type of monitoring and control mechanism may be desirable to insure the substantially complete oxidation of the organics. One known control mechanism for electrolysis operation which could be adapted to this application is based on the measurement of oxidation reduction potential (OPR) in the sample after the reactor. Alternatively, the dissolved oxygen concentration in the sample after the reactor could be monitored.

DETAILED DESCRIPTION OF PREFERRED EMBODIMENTS

Figure 1:
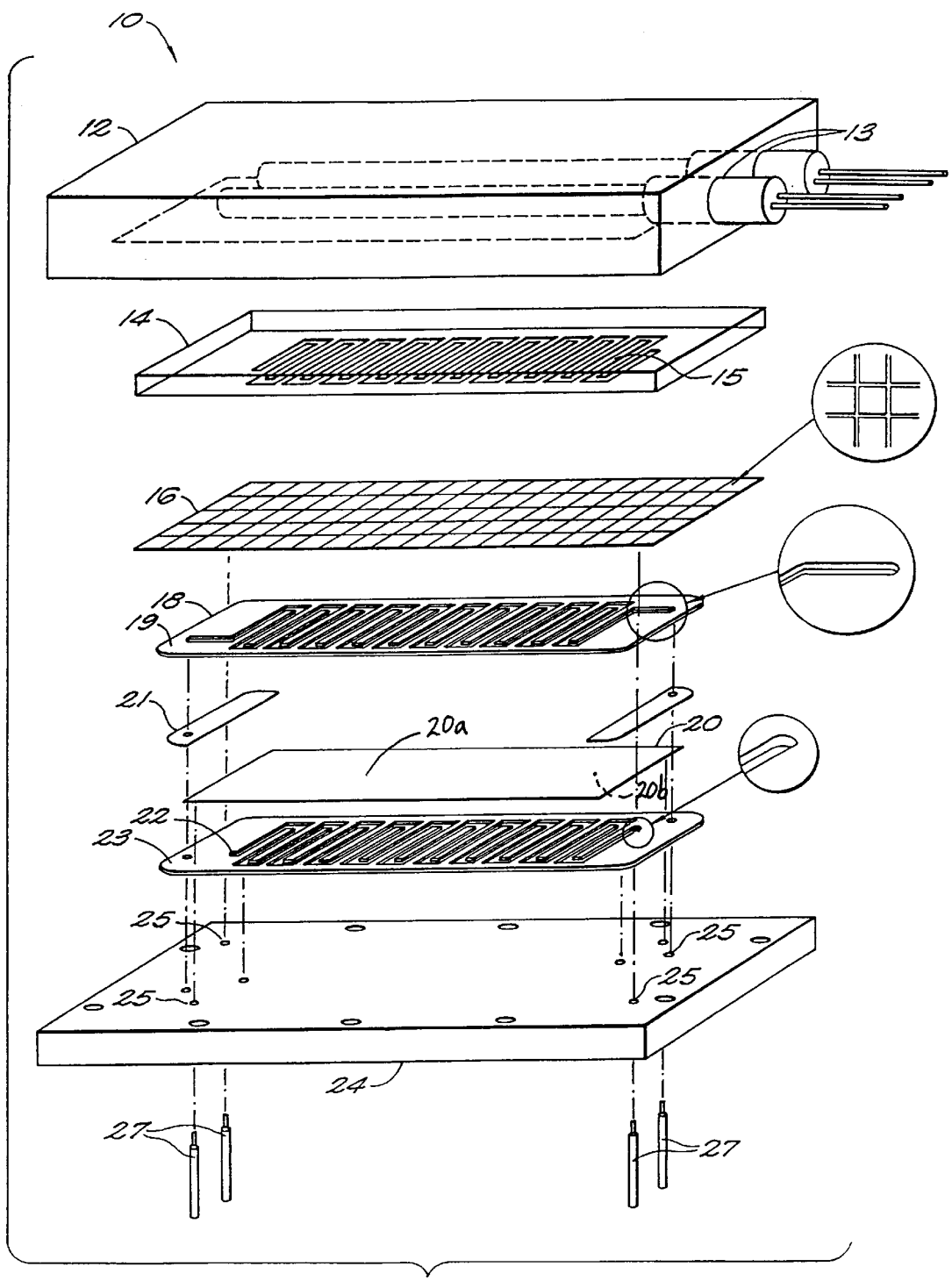
FIG. 1 is an exploded schematic view of the reactor of the present invention.

A schematic of an embodiment of an oxidation reactor 10 which may be used in the practice of this invention is shown in FIG. 1. There are seven basic components for oxidation reactor 10: U.V. lamps and housing 12; fused silica window 14; wire-mesh anode 16 of titanium, platinum, gold or other suitable material; ceramic sample chamber 18; a bielectrode (which may function as a cathode in the primary oxidation electrolysis cell and as an anode in the secondary electrolysis cell) 20; second ceramic sample chamber 22; and a stainless steel pressure plate 24. A more detailed description of these components is set forth below.

Two low-pressure mercury vapor lamps 13 are located in a stainless steel housing 12 positioned above the sample chamber 18. The lamp emits radiation at both 254 nm and 184 nm. The short wavelength radiation produces hydroxyl radicals from the photolysis of water for the oxidation of organic compounds. The housing 12 is also equipped with a view port (not shown) to permit inspection of the inside of the reactor.

While these lamps are commonly used for photochemical oxidation, the lamps only emit a small fraction (about 3%) of radiation in the short wavelength region (185 nm). Recently new lamps have been developed with high intensity emissions in the vacuum ultraviolet (175–210 nm), the wavelength region favorable for the formation of $O_3$, $H_2O_2$ and OH. Xenon-doped mercury lamps have a maximum intensity in the 210 to 230 nm region. Krypton chloride excimer lamps emit at 222±6 nm and Xenon excimer lamps have a maximum emission at 172±nm. The use of these UV sources in the oxidation reactor increases the amount of oxidizing agents produced photochemically and improves the oxidation efficiency compared with the Hg vapor lamps. Another advantage of these lamps compared with the Hg vapor unit, particularly for space-based applications, is the elimination of the toxic element mercury. To avoid potential leakage and exposure to Hg, triple containment systems are typically required for Hg vapor lamps. Using Xe excimer lamps eliminates these special containment requirements and provides more efficient generation of oxidizing agents.

A fused silica window 14 is located below the lamps 13 to provide a liquid-tight seal, yet permit transmission of the UV radiation to the sample chamber 18. To limit the exposure of UV radiation to the sample chamber 18 and avoid exposing other components of the reactor to UV, an anode mask 15 formed from the deposition of a Pt or similar metal or alloy on the fused silica is employed. This thin layer of Pt alloy is deposited to define a serpentine pattern identical to that of the sample chamber 18. The mask is not part of the electrical system, but simply limits the transmission of UV light to the sample chamber 18, preventing possible oxidation of other components of the reactor.

Positioned below the fused silica window 14 is the wire mesh anode 16. The anode is a flat piece, with the wire mesh formed by etching the metal, rather than weaving the wire. The wire anode in the preferred embodiment is 0.025 mm thick, with 0.23 mm×0.23 mm square holes etched into the metal to permit transmission of UV light to the sample chamber 18. Use of the wire anode provides electrochemical production of oxygen from water and combined with the intense short wave UV light provides for the oxidation of organic compounds.

A ceramic spacer 19 with a laser cut serpentine pattern is used to define the sample chamber 18 to contain the sample. The spacer in the preferred embodiment is composed of 99.9% $Al_2O_3$ and the serpentine flow channel is 2.1 mm wide×0.4 mm deep with a calculated volume of 0.76 mL.

Positioned below the sample chamber is the cathode 20. The cathode material in the preferred embodiment is a 0.13 mm thick Pd/Ag alloy (25% Ag). The cathode is electrically isolated from the stainless steel housing of the reactor by means of two TEFZEL ethylene-tetrafluoroethylene copolymer type material spacers 21.

Positioned below the cathode 20 is a sheet of TEFZEL brand from DuPont ethylene-tetrafluoroethylene copolymer type material 23, 0.48 mm thick, with a serpentine pattern cut into the spacer. The chamber 22 is filled with liquid and used as a second electrolysis cell. After the concentration of $CO_2$ in the outlet stream of the primary oxidation reactor is measured using the membrane-based $CO_2$ sensor, the waste stream is then passed back through the chamber 22, as shown in the schematic drawing of FIG. 3. As will be described in more detail below, the waste stream is used to generate oxygen and hydrogen electrolytically. The goal is to rapidly remove hydrogen from the primary oxidation reactor by reacting it with oxygen produced in the second electrolysis cell.

The reactor is sealed by means of a stainless steel pressure plate 24 which also serves as one of the electrodes (cathode) for the second electrolysis cell. As shown in FIG. 1, the stainless steel pressure plate 24 and the spacers 21 are fitted with holes 25 to provide electrical contact to the cathode and the anode. Metal pins 27 are inserted through the holes at opposite edges of the pressure plate and contact the edges of the cathode and the anode. The wire anode 16 is slightly larger than the ceramic spacer 19 and cathode 20. The metal pins 27 can therefore be inserted through the pressure plate 24 (not touching it) to contact the wire anode 16 (again at opposite corners) without touching the cathode 20 to provide the electrical contact to the anode 16.

Figure 2:
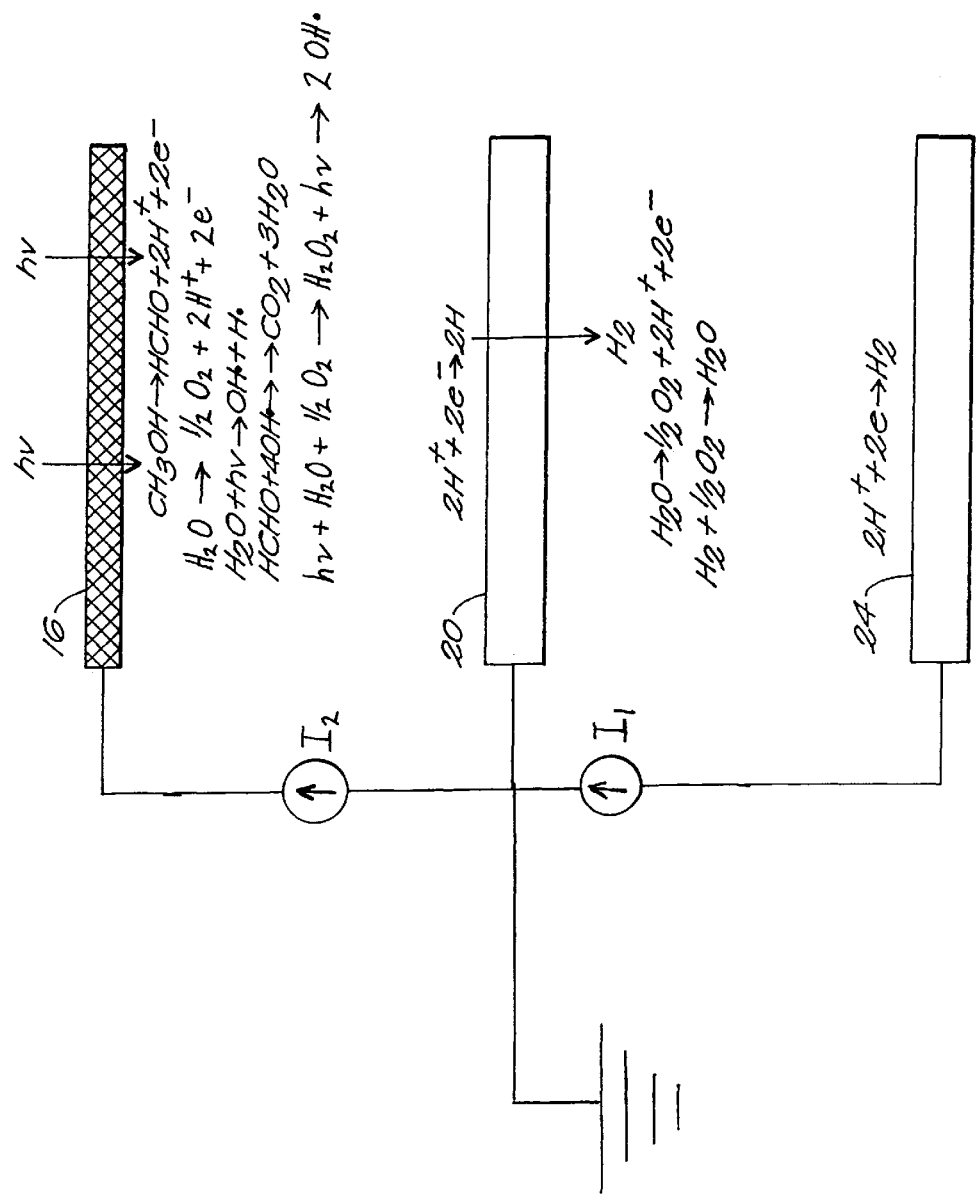
FIG. 2 is a schematic diagram of the electrical oxidation reactor of the present invention.

A schematic of the power supply used for these experiments is shown in FIG. 2. The system provides two independent constant current supplies, one for the primary oxidation cell and the second for the electrolysis of water to produce oxygen in the chamber 22. The cell currents can be independently adjusted, but typically the primary oxidation cell is operated at about 5 mA and the secondary cell is operated at about 10 mA.

FIG. 2 also shows the three electrodes. Electrode 16 is the wire anode 16 of the primary oxidation cell; electrode 20 may be, for example, a Pd/Ag alloy "bielectrode" 20 of the primary oxidation cell; and electrode 24 is the stainless steel pressure plate 24. As shown in FIG. 2, electrode 20 is connected to ground, that is a common current return, not the case of the reactor. Electrode 16 is operated at a sufficiently positive potential so that in the primary oxidation cell, the Pd/Ag alloy (electrode 20) is the cathode and the wire (electrode 16) is the anode. However, electrode 24 is operated at a sufficiently negative potential so that in the secondary electrolysis cell, the stainless steel pressure plate (electrode 24) is the cathode and electrode 20 is the anode.

The system is better understood in terms of the reactions occurring at the electrodes. In the primary oxidation cell, oxidation of the organic compounds and possibly production of oxygen from water occurs at the wire electrode 16. Photolytic oxidation of organic compounds can also occur in the primary oxidation cell. Reduction of hydronium ions to form $H_2$ or hydrogen atoms occurs at the Pd/Ag electrode 20. On the secondary electrolysis chamber side of electrode 20, oxidation of water to produce oxygen is the desired reaction, while reduction of hydronium ions to produce $H_2$ occurs at electrode 24.

Since the Pd/Ag alloy electrode is permeable to H atoms, the goal is to have hydrogen produced in the primary reactor diffuse through the Pd/Ag alloy. At the metal/solution interface of the secondary electrolysis cell, the hydrogen will encounter electrolytically produced oxygen from water and be effectively removed from the system by forming water. Whatever reactions are occurring, the basic idea is to facilitate removal of hydrogen from the primary oxidation cell.

Figure 3:
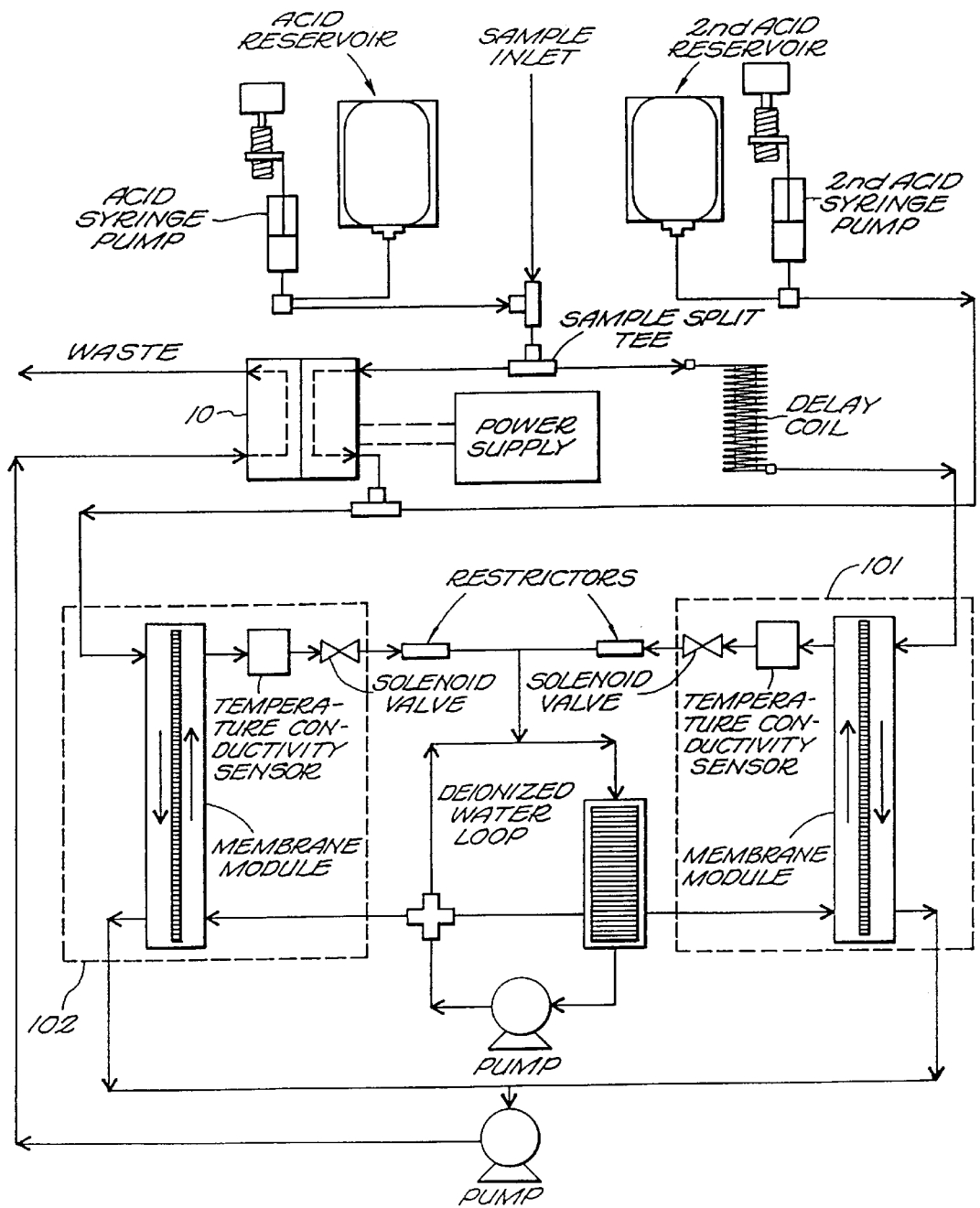
FIG. 3 is a block diagram depicting an embodiment of the present invention for the on-line measurement of both total organic and inorganic carbon concentrations, employing a stream splitting technique.

The oxidation reactor 10 may be used in a TOC detector, such as Sievers Instruments Model 800 TOC analyzer. The normal oxidation reactor is removed from the system and the "Reagentless Oxidation Reactor 10" is installed. A schematic of the apparatus as so modified is shown in FIG. 3. A variable speed peristaltic sampling pump is used to draw sample into the instrument, typically at a flow rate of 0.28 mL/min. As shown in FIG. 3, the sample stream is split into two channels; Total Inorganic Carbon (TIC) and Total Carbon (TC). In operation, the sample stream is acidified with 6 M $H_2PO_4$ to pH <2 and then split. Half of the stream flows through a delay coil (without any oxidation) and into a membrane-based $CO_2$ sensor 101 for the measurement of total inorganic carbon ($HCO_3^-$ and $CO_3^{-2}$) in the sample. The rest of the sample flows through the oxidation reactor 10 and into a second membrane-based $CO_2$ sensor 102 for the measurement of total carbon content (TC=TIC+TOC). TOC is then computed from the difference. (TOC=TC−TIC).

Operation of the membrane-based $CO_2$ sensors is based on the diffusion of $CO_2$ from the acidified sample stream, across a gas permeable membrane into a thin layer of deionized water. In the deionized water, the $CO_2$ will ionize to form $H^+$ and $HCO_3^-$. As the sample stream flows continuously through the membrane module, the concentration of $CO_2$ on both sides of the membrane will approach an equilibrium. The conductivity of the deionized water can then be measured and the concentration of $CO_2$ in the sample stream determined. As shown in FIG. 3, deionized water is continuously produced by means of circulation pump and a mixed bed of ion exchange resin.

EXAMPLE I

Five compounds were selected for testing with the reactor and are listed in Table I. They represent compounds that are relatively easy to oxidize (methanol, ethanol and KHP), and compounds that should be difficult to oxidize (trichloroethylene and urea).

TABLE I

| Compounds Selected for Testing of Oxidation Reactor | |
|---|---|
| Potassium hydrogen phthalate (KHP) | Methanol |
| Ethanol | Urea |
| Trichloroethylene | |

Standard solutions of the test compounds were prepared in low TOC, deionized water at 10–50 mg/L C. The concentrations of these standard solutions were checked by measurement of TOC using a Sievers Instruments Model 800 TOC Analyzer with UV/persulfate oxidation.

Figure 4:
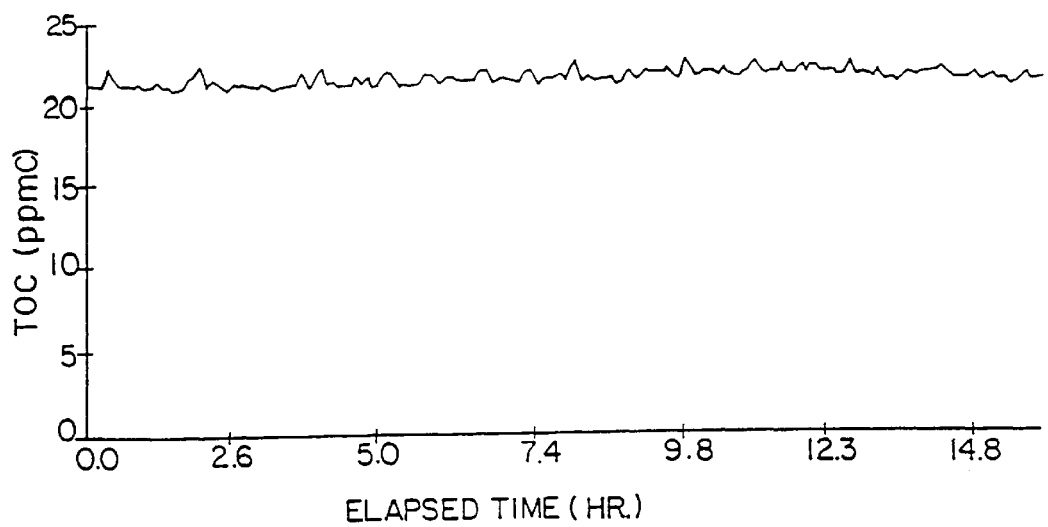
FIG. 4 is a chart showing test results on the reactor of the present invention.

After the reactor clean-up, the performance of the reactor for the oxidation of a standard solution of potassium hydrogen phthalate (KHP) at about 25 ppm C was determined. A plot of the measured TOC versus time is shown in FIG. 4. The purpose of this experiment was simply to establish operating conditions for the electrolysis cells, but as shown in FIG. 4, the reactor operated for 16 hours without any significant decrease in oxidation efficiency.

In the experimental set-up, the reactor is not enclosed or thermostated, but heat from the UV lamps and the electrolysis cells increases the temperature of the outside of the reactor to >30° C. All of the preliminary experiments were performed at these elevated temperatures.

Figure 5:
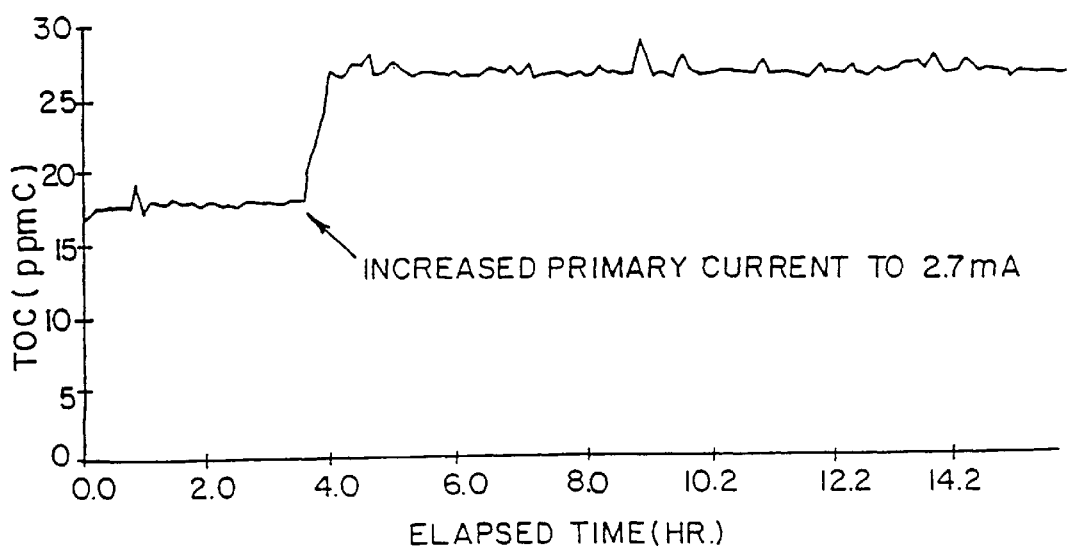
FIG. 5 is a chart showing test results on the reactor of the present invention.

The oxidation efficiency for a standard solution of KHP (28.6 mg/L C) was determined as a function of applied current and the results from this test are shown in FIG. 5. Initially, the primary oxidation cell was operated at an applied current of 1.7 mA and the secondary cell operated at 3 mA. The residence time of the sample in the reactor was 5.6 minutes. Under these conditions, the oxidation efficiency was only 63%, but no decrease in performance was observed. The current for the primary cell was then increased to 2.7 mA and the secondary cell current increased to 4.1 mA. The oxidation efficiency at the higher current increased to 93% and the oxidation efficiency remained relatively constant at the higher current for about 12 hours of continuous operation.

EXAMPLE II

A possible obstacle to the complete oxidation of organics to $CO_2$ is the reduction of $CO_2$ in the reactor. When a standard solution of $Na_2CO_3$ was passed through an earlier reactor design that did not have the secondary electrolysis chamber, the response of the $CO_2$ sensor was 10–15% lower than expected, and it was determined that $CO_2$ was being electrolytically reduced in the reactor. Therefore, an experiment was performed with the present invention to analyze a 25 mg/L C solution of $Na_2CO_3$. Analysis of the solution with the electrolysis cells and UV lamps off gave an average TC value of 25.2 mg/L. When the electrolysis cells were turned on, but with the UV lamps off, the average TC value was 25.3 mg/L. Analysis of this solution with both electrolysis and UV lamps on gave an average TC value of 24.9 mg/L. The results from these experiments suggest that reduction of $CO_2$ is not occurring to any significant degree in the new reactor design. The more effective hydrogen removal from the primary oxidation reactor using the secondary electrolysis chamber for hydrogen removal prevented the reduction of $CO_2$ in the primary oxidation reactor.

EXAMPLE III

A preliminary investigation of the effect of residence time in the reactor (i.e. sample flow rate) on the oxidation efficiency was performed. The 30.5 mg/L C KHP standard was analyzed for about 9 hours with a reactor residence time of 5.5 minutes (primary current=4.6 mA, secondary current= 10 mA), then the flow rate was decreased to give a residence time of 7.2 min. using the same reactor currents. The rate of addition of acid was also changed to maintain the same pH for the sample stream at the lower sample flow rates. At the shorter residence time (5.5 min.) the oxidation efficiency was 95% (TOC=29.6±0.2 mg/L). Increasing the residence time to 7.2 minutes gave an average oxidation efficiency of 99.5% (TOC=30.4±0.3 mg/L).

Figure 6:
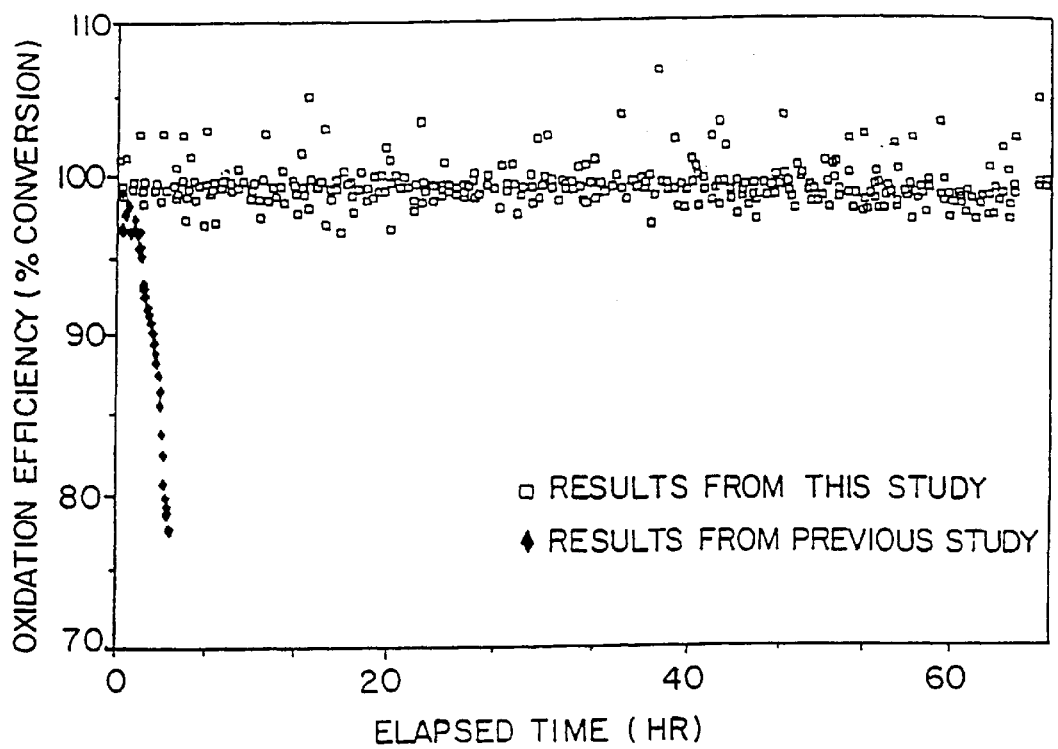
FIG. 6 is a chart showing the oxidation efficiency of the oxidation reactor of the present invention over time.

To determine if this higher oxidation efficiency at the longer residence time could be sustained, the 30.5 mg/L CKHP standard was run for about 64 hours (primary current=4.6 mA, secondary current=10 mA, residence time= 7.2 min.) and the results are shown in FIG. 6, along with the best results achieved in a previous study using no secondary electrolysis hydrogen removal chamber.

The oxidation efficiency of the new reactor was stable for this 66 hour test, with an average efficiency of 99.3% (TOC=30.3±0.3 mg/L). In contrast, the best results from a previous study showed stable performance for only about 1.5 hours, followed by a precipitous drop-off in oxidation efficiency.

The improved performance of the new reactor design is most likely due to a combination of factors. The wire mesh anode has a significantly larger surface area than the anode used in the original reactor design. The large anode area results in improved electrolytic oxidation. The new reactor design also permits more efficient removal of hydrogen from the reactor. In the new design, hydrogen production appears to be distributed more uniformly across the Pd/Ag alloy. It is clear that there is no build-up of hydrogen in the Pd/Ag alloy membrane utilized in this example. If hydrogen was building up in the membrane, past experiments have shown that the membrane would swell as much as 200% in volume. In this example, however, the Pd/Ag alloy member showed substantially no change in volume. Finally, the use of the secondary electrolysis cell improves the removal of hydrogen from the Pd/Ag alloy preventing hydrogen build-up in the primary oxidation electrolysis chamber.

EXAMPLE IV

The efficiency of the reactor for the oxidation of a 45.7 mg/L C solution of ethanol was determined at three different flow rates and the results from this test are shown in Table II. All experiments were performed with a primary current of 5.1 mA and a secondary current of 11.4 mA. In contrast with the experiments described above, a fan was used to cool the outside of the reactor to about 27° C. Oxidation efficiency increased with increasing residence time; however, the oxidation efficiency was reduced at the lower reactor temperature.

TABLE II

Oxidation Efficiency versus Reactor Residence Time for 45.7 ppm C Ethanol at 27° C.

| Reactor Residence Time (min) | Oxidation Efficiency |
|---|---|
| 10 | 63% |
| 15 | 87% |
| 20 | 97% |

EXAMPLE V

As noted above, lower oxidation efficiency was observed when the reactor was cooled. The rate of most chemical reactions will increase as the temperature is raised, typically doubling for each 10° C. increase in temperature. Thus, one would expect higher oxidation efficiencies at higher temperatures. The situation regarding removal of hydrogen from the reactor using the Pd/Ag alloy is more complicated. The diffusion of hydrogen atoms through Pd and Pd/Ag alloys increases with increasing temperature. However, the solubility of hydrogen in these materials decreases with increasing temperatures. Calculations indicate that overall permeation of hydrogen should increase with increasing temperatures and therefore a series of experiments were performed to determine if better efficiencies could be obtained at higher reactor temperatures.

Figure 7:
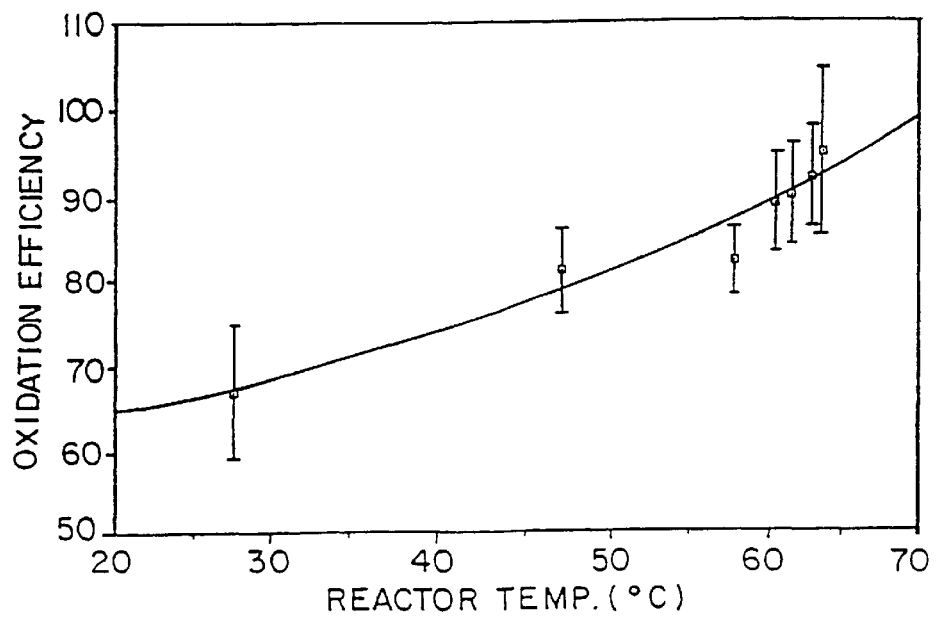
FIG. 7 is a chart showing the oxidation efficiency of the oxidation reactor of the present invention compared to reactor temperature.

For these experiments, a fan was used initially to cool the reactor, with applied currents of 5.1 mA for the primary and 11 mA for the secondary cell, with a residence time of 15 min. The fan was then turned off and the temperature of the reactor allowed to rise. The reactor was not thermostated, rather the temperature of the outside of the reactor was monitored and an "average" temperature and TOC determined as the reactor warmed. Finally, the reactor was insulated to obtain temperatures above 60° C. The results from this experiment are shown in FIG. 7.

The oxidation efficiency increased from 75% to 95% as the temperature of the reactor increased. The error bars are ± one standard deviation and the wide range in the measurements is most likely due to changing temperatures during the course of this experiment.

The result from this experiment indicates that the best oxidation efficiency will be obtained at higher temperatures. The present design does not permit heating of the reactor, but a temperature of about 60° C. can be maintained by insulating the reactor.

Using the insulated reactor, one can determine the oxidation efficiency as a function of reactor residence time for three of the test compounds, trichloroethylene, urea and methanol. These experiments were performed at a 5 mA current for the primary cell and 11 mA for the secondary cell. The results from these tests are shown in Table III. Using a 20 minute residence time and a reactor temperature of about 60° C., an oxidation efficiency of 96% was achieved for urea and 97% for trichloroethylene. For methanol, an 88% oxidation efficiency was obtained for a 7 min. reactor residence time and 99% oxidation was obtained at 20 min. residence time.

If one assumes that the rate of the oxidation reactions is independent of the concentration of oxidizing agents then the rate of the oxidation is simply rate of oxidation=$k^1$[organic compound]

where $K^1$ is a pseudo first order rate constant. Using the results from Table 111, one can calculate the pseudo first order rate constant and these values are shown in Table IV.

The pseudo first order rate constant for ethanol and urea at 27° C. are larger than the recently reported oxidation rate constants using ozone and hydrogen peroxide for large scale oxidation of organic compounds in water. For the oxidation of urea, Verostko et al., measured $k^1$ of 0.003/min. The 0.06/min. value obtained in this study using the present invention reflects the rapid oxidation that can be achieved using combined photolytic and electrolytic oxidation at elevated temperatures.

At the higher reactor temperature, an approximately three fold increase in the rate of the reaction was observed. The important factor in using this reactor for TOC measurements is the residence time in the reactor required to achieve complete oxidation. Based on half life measurements, increasing the reactor temperature greatly decreased the amount of time required for 50% oxidation and operating at the higher temperature provides a more reasonable measurement time for TOC analysis.

TABLE III

Performance of Oxidation Reactor at Elevated Temperatures

| Compound | Oxidation Efficiency Residence Time (min.) | | | |
|---|---|---|---|---|
| | 7.2 | 10 | 15 | 20 |
| Urea (42.5 ppm C.) | — | 58% | 70% | 96% |
| Trichloroethylene (20.2 ppm C.) | — | — | — | 97% |
| Methanol (46.2 ppm C.) | 88% | 97% | 98% | 99% |

TABLE IV

Pseudo First Order Rate Constants and Half Lifes

| Compound | $k^1$(min.$^{-1}$) | $t_{1/2}$(min.)* |
|---|---|---|
| Urea (60° C.) | 0.06 | 12 |
| Methanol (60° C.) | 0.13 | 5 |
| Ethanol (27° C.) | 0.08 | 8 |
| Urea (27° C.) | 0.02 | 35 |

*$t_{1/2} = (1/k^1) \ln 2$

Simplified Invention Practice

In a first embodiment of the simplified practice of the applicants' invention for in situ generation or enhancement of oxidizing conditions for promoting oxidation of organic compounds in aqueous samples for subsequent carbon measurement, an apparatus comparable to that illustrated in FIG. 1 may be utilized. For purposes of the first embodiment of the simplified practice of this invention, the only required adaptations to the FIG. 1 apparatus would be to turn off or disconnect electrical power to electrodes 16, 20 and 24. Alternatively, a simplified apparatus constructed to carry out this first embodiment of the simplified invention practice might consist solely of sample/reaction chamber or oxidation cell 18, positioned in proximity to an energy source capable of providing energy to the sample, such as U.V. lamp 13, and an inorganic hydrogen-absorbing member 20. Hydrogen-absorbing member 20 is preferably selected from the so-called "transition" metals or elements (groups III B, IV B, V B, VI B, VII B, VIII, and I B of the periodic table of elements) and alloys thereof, most preferably selected from the group of metals and metal alloys consisting of palladium, palladium alloys, titanium, titanium alloys, platinum, platinum alloys, and nickel and nickel alloys. Other inorganic materials capable of absorbing hydrogen could be used, however. If the energy source is a U.V. lamp, it is desirable to also include the fused silica window 14 shown in FIG. 1 in this embodiment. Alternative suitable sources for providing energy to the sample in the chamber/oxidation cell 18 might include electrochemical means, temperature means, ultrasonic means, and radioactive means.

The method for utilizing an adaptation of the apparatus of FIG. 1 to carry out the first embodiment of the simplified invention practice will now be described. It will be apparent that substantially the same method is utilized for operating the alternative, simplified apparatus described above. First, no external electrical power would be supplied to electrodes 16, 20 and 24 in FIG. 1. Second, instead of continuously flowing an aqueous sample into and through sample/reaction chamber or oxidation cell 18, the simplified invention practice may be run on either a batch or flowing sample.

Thus, an aqueous sample containing organic compounds is flowed into sample/reaction chamber 18. While contained in chamber 18, energy is provided to the sample, for example by means of U.V. light from a U.V. lamp 13, and at least a portion of the sample in chamber 18 is brought into direct physical contact with a portion of one (i.e., the upper) face or surface 20a of inorganic hydrogen-absorbing member 20. In a surprising and completely unexpected development, it has been found in accordance with this embodiment of the invention that, under the above-described conditions, and even without establishing any electrical field, that the oxidation of the organic compounds in the sample to carbon dioxide will be facilitated and increased. Specifically, it has been found that this embodiment of the invention, wherein an aqueous sample is exposed to U.V. light in chamber 18 and is contacted with an inorganic hydrogen-absorbing member 20, results in being able to substantially completely oxidize two times the concentration of methanol in the sample that could be so oxidized using a conventional coiled quartz reactor and U.V. light (no hydrogen-absorbing member). These results are discussed hereinafter in Example VI and Table V. It is believed that the mechanism here at work is that the hydrogen absorption member 20 absorbs hydrogen from the aqueous sample thereby creating, in situ, and without addition of oxidizing agents or oxygen, an enhanced oxidizing environment in the sample. In conjunction with a supply of energy to the sample in chamber 18, for example in the form of U.V. light, such an in situ-generated oxidizing environment promotes oxidation of organic compounds to carbon dioxide, which then can be detected and measured utilizing any $CO_2$ sensor or, more particularly, the conductivity cell technology of this invention.

It has been found that the first simplified embodiment of the in situ technology, as described above, is most effective in situations where there is a relatively low concentration of organic compounds in the aqueous sample. The ability to provide an in situ-generated oxidizing environment is thought to be limited by the ability of face 20a of hydrogen-absorbing member 20 to absorb and retain hydrogen along and adjacent the absorption surface. Accordingly, this first simplified embodiment appears to operate best when oxidation requirements for the sample are relatively small. Following oxidation of organic compounds in the aqueous sample in chamber 18, that sample is sent to a carbon dioxide sensor, and chamber 18 is then converted to operate in a hydrogen desorption/regeneration cycle in which the chamber is flushed with fresh water, an aqueous liquid such as deionized water, or similar cleansing fluid for a period sufficient to substantially completely remove absorbed hydrogen from face 20a of absorption member 20, thereby restoring the absorption surface for use in another absorption cycle.

In a variation of this invention embodiment. electrodes 16 and 20 as shown in FIG. 1 may be connected to electrical power supplies so as to have wire mesh member 16 function as a cathode and absorbing member 20 function as an anode during the hydrogen desorption cycle. Such "reverse" polarization of electrodes 16 and 20 (i.e., polarization opposite to that utilized in connection with previously described embodiments of this invention) has been found to speed up and facilitate the removal of absorbed hydrogen from face 20a of electrode 20, or from the bulk material of member 20, thereby more quickly and completely preparing this apparatus for another cycle of oxidizing organic compounds in another aqueous sample. It will be appreciated that the foregoing "reverse" polarization procedure for facilitating the hydrogen desorption/regeneration cycle cannot be utilized in the above-described simplified (non-FIG. 1) apparatus configuration unless that simplified apparatus further includes at least a second electrode, such as wire mesh electrode 16, disposed along a different portion of sample chamber 18 and separated from hydrogen-absorbing electrode 20 by the fluid contained in chamber 18. The "reverse" polarization procedure further requires electrical connection means from an electrical power source to each of electrodes 16 and 20. Those apparatus elements are, of course, already present when the apparatus of FIG. 1 is adapted to this alternative mode of operation.

A second embodiment of the simplified practice of the applicants' invention for in situ generation of oxidizing conditions for promoting oxidation of organic compounds in aqueous samples utilizes a first polarization of electrodes 16 and 20 as shown in FIG. 1 across sample chamber 18 during the hydrogen absorption cycle, and a "reverse" polarization of electrodes 16 and 20 during the hydrogen desorption/regeneration cycle. For carrying out this second simplified practice of the applicants' invention, the apparatus of FIG. 1 may be adapted by turning off or disconnecting electrical power to electrode 24. Alternatively, a simplified apparatus to carry out this second embodiment of the simplified invention practice might consist solely of sample chamber 18, positioned in proximity to an energy source capable of providing energy to the sample, such as U.V. lamp 13, an inorganic hydrogen-absorbing electrode 20, as previously described, and a second electrode, such as wire mesh electrode 16, disposed along a different portion of sample chamber 18 and separated from absorption electrode 20 by the fluid contained in chamber 18, together with electrical connection means from an electrical power source to each of electrodes 16 and 20.

The method for utilizing an adaptation of the apparatus of FIG. 1 to carry out the second embodiment of the simplified invention practice will now be described. It will be apparent that substantially the same method is utilized for operating the alternative, simplified apparatus described above for this second embodiment. First, no external electrical power would be supplied to electrode 24 in FIG. 1, and, indeed, no secondary electrolysis chamber would be required. Second, instead of continuously flowing an aqueous sample into and through sample chamber 18, the simplified invention practice may be run on either a batch or flowing sample basis. Instead of hydrogen being drawn through electrode 20 and removed in a second electrolytic cell, as earlier described, in this embodiment of the invention hydrogen is periodically removed from electrode 20 using chamber 18.

Thus, an aqueous sample containing organic compounds is flowed into sample chamber 18. While contained in chamber 18, the sample is exposed to an energy source, such as to U.V. light from a U.V. lamp 13. At the same time, electrical power is supplied by electrical connection means from an external electrical power source to inorganic hydrogen-absorbing electrode 20 and to electrode 16 such that electrode 16 operates as an anode and electrode 20 operates as a cathode. At least a portion of the sample in chamber 18 is brought into direct physical contact with a portion of one (i.e., the upper) face or surface 20a of absorbing electrode 20. The electrical field thus established between electrodes 16 and 20 is believed to assist in splitting water and attracting hydrogen from the aqueous sample to face 20a of electrode 20, as well as in either holding it to said face 20a or, perhaps, in diffusing a portion of the hydrogen into the interior interstices of absorbing electrode 20, thereby creating, in situ, an oxygen-enriched environment in the sample. In the absence of electrical power also being supplied to electrode 24 to establish electrode 24 as a cathode relative to face 20b of electrode 20 (as earlier described in connection with another embodiment of this invention), however, little or none of the hydrogen absorbed on face 20a or diffused into electrode 20 will be drawn through electrode 20 and out through the face 20b opposite face 20a.

In conjunction with a supply of energy to the sample in chamber 18, for example in the form of U.V. light, the in situ-generated oxidizing environment promotes oxidation of organic compounds to carbon dioxide, which then can be detected and measured utilizing the $CO_2$ sensor technology of this invention. It has been found that the use of electrical polarization of the electrodes during the hydrogen absorption cycle facilitates more rapid oxidation of organic compounds in the sample to carbon dioxide, presumably because of a higher level of oxygen-enrichment in the sample. The use of electrical polarization of the electrodes during the hydrogen absorption cycle thus permits this second embodiment of the simplified invention practice to be effectively utilized with relatively higher concentrations of organic compounds in the aqueous sample. In this embodiment, it is believed that oxygen is electrolytically split from water in the aqueous sample, while the hydrogen formed thereby is removed from the sample by being absorbed onto or diffused into the hydrogen-absorbing cathode material.

Following oxidation of organic compounds in the aqueous sample in chamber 18, that sample is sent to a carbon dioxide sensor. Chamber 18 may then be converted to operate in a hydrogen desorption/regeneration cycle. The hydrogen desorption/regeneration cycle may be assisted by either flushing the surface 20a of electrode 20 with a cleansing fluid, such as fresh, low-hydrogen containing water, or by reversing the polarity of electrodes 16 and 20 for a period of time, or by a combination of these two processes. The purpose of either process, or a combination of both, is to remove hydrogen from the surface and/or the bulk interior of the inorganic hydrogen-absorbing member 20. Alternatively, as described below, it may also be possible in this second embodiment to reuse chamber 18 for another aqueous sample without an intermediate hydrogen desorption/regeneration cycle.

Thus, in the first embodiment of the simplified invention practice (i.e., without electrical polarization of electrodes during hydrogen absorption), it is sometimes (although not always) necessary to alternate each hydrogen absorption cycle with a hydrogen desorption/regeneration cycle before commencing a new hydrogen absorption/oxidation cycle for a new aqueous sample. This is believed to be because of the relatively limited capacity of the inorganic hydrogen-absorbing member to absorb and retain hydrogen in the absence of an electrical field. If the organic compounds are present in the aqueous samples in relatively low concentrations however, especially relative to dissolved oxygen in the sample and/or in combination with low hydrogen concentrations, then it may be possible to run several sequential samples using the first simplified embodiment without intermediate hydrogen desorption cycles. On the other hand, with the second (electrical polarization of electrodes) embodiment of the simplified invention practice, it has been found that, depending on the concentration of organic compounds in the aqueous samples, it is commonly possible and highly desirable to run two or more aqueous samples in sequence, or to run the samples continuously, without an intermediate hydrogen desorption/regeneration cycle. This leads to faster and more efficient measurements of carbon in the aqueous samples. It is believed that the application of an electrical field between absorbing electrode 20, operated as a cathode, and another electrode, such as electrode 16, operated as an anode, results in either more effectively holding hydrogen along face 20$a$ or, probably, in causing at least a portion of the hydrogen to diffuse into the interior of electrode 20, in either case resulting in greater oxygen enhancement in the sample. Depending on the level of oxygen generation in the aqueous sample required to substantially completely oxidize the organic compounds to carbon dioxide, at some point the completeness of the oxidation will decrease as shown in FIG. 6 and as discussed in reference to that figure and the related example. Thus, in one example, 43 ppm of organic compounds (as carbon) were oxidized at substantially 100% efficiency for a period of about one and one-half hours, after which recovery began to decrease.

In a preferred variation of this second embodiment of the simplified invention practice, when the time comes for a hydrogen desorption cycle, it is facilitated by reversing the electrical polarities of electrodes 16 and 20. Thus, during a hydrogen desorption/regeneration cycle, absorbing electrode 20 will be operated as an anode and electrode 16 will be operated as a cathode. Such "reverse" polarization of electrodes 16 and 20 has been found to speed up and facilitate the removal of absorbed hydrogen from face 20$a$, as well as from the interior, of electrode 20, thereby regenerating and restoring the electrode 20 as an efficient hydrogen-absorbing member, and preparing this apparatus for oxidizing organic compounds in a subsequent sequence of aqueous samples. This "reverse" polarization mode may be utilized with or without separate flushing of the absorption surface as previously described. Instead, a continuous or pulsed flow of the aqueous sample may be used to sweep desorbed hydrogen out of the sample/reaction chamber. Following a complete hydrogen desorption/regeneration cycle, the system is ready for maximum oxidation recovery in new aqueous samples due to the renewed ability of the hydrogen-absorbing member to remove excess hydrogen, produced from the electrolysis and/or photolysis of water, from the new samples. Thus, this alternation between hydrogen absorption cycles and periodic desorption/regeneration cycles allows oxidation of organics in aqueous samples to be resumed at substantially 100% efficiency by controlling the relative timing (duration) of the respective absorption and desorption cycles.

The following examples of the several embodiments of the simplified practice of this invention will further illustrate the operation and advantages of these embodiments.

One example of an embodiment of the simplified invention practice is based on the data presented above in Example III and as shown in FIG. 6 as "Results from previous study." In this previous study, no secondary electrolysis hydrogen removal chamber was utilized. A 43 ppm aqueous solution of methanol was flowed through the oxidation reactor where it contacted a surface of a palladium absorption electrode operated as a cathode for a water-splitting electrolysis cell during a hydrogen absorption cycle. In the oxidation reactor the methanol solution was also exposed to U.V. light.

The data in FIG. 6 shows that, for a period of about 1.5 hours, this system achieved close to 100% oxidation of the methanol to carbon dioxide. During the period of about 1.5 to 2 hours, however, there was a precipitous drop-off in oxidation efficiency, believed to represent the loss of the ability of the palladium absorption electrode to absorb additional hydrogen. At this point, the hydrogen absorption cycle was stopped by stopping the flow of methanol solution. Instead, low hydrogen-containing water was flowed through the oxidation reactor as a wash fluid, and the electrical polarity of the electrodes was reversed such that the palladium hydrogen-absorbing electrode operated as an anode, resulting in the absorbed hydrogen being desorbed.

After running this hydrogen desorption cycle for a period of 10 minutes, the polarity of the electrodes was again reversed (back to the mode in which the absorption electrode operates as a cathode) and the flow of methanol solution to the oxidation reactor was resumed. It was found that the oxidation reactor had been restored to substantially 100% oxidation efficiency by the relatively brief hydrogen desorption cycle. Once again, oxidation efficiency was found to remain relatively constant at close to 100% for about 1.5 hours, before another precipitous drop-off occurred. Again, however, a 10 minute hydrogen desorption cycle regenerated the palladium absorption electrode so that the reactor was again restored to almost 100% efficiency. This cycle was repeated multiple times without any loss in the reactor's oxidation efficiency following a brief hydrogen desorption/regeneration cycle.

EXAMPLE VI

In another set of experiments, the efficiency of the oxidation reactor (photo-oxidation only) for the conversion of a standard solution of methanol (4 ppm C) without the presence of inorganic carbon was determined.

TABLE V

| EFFICIENCY OF OXIDATION REACTOR FOR THE PHOTO-OXIDATION OF METHANOL | | | |
| --- | --- | --- | --- |
| MEASUREMENT # | TIME (min.) | TOTAL CARBON (ppm C) | % of Final Response |
| 1 | 0 | 0.04 | 1 |
| 2 | 5.8 | 1.44 | 43 |
| 3 | 11.4 | 2.47 | 74 |
| 4 | 17.2 | 2.99 | 90 |

TABLE V-continued

EFFICIENCY OF OXIDATION REACTOR FOR
THE PHOTO-OXIDATION OF METHANOL

| MEASUREMENT # | TIME (min.) | TOTAL CARBON (ppm C) | % of Final Response |
|---|---|---|---|
| 5 | 23.0 | 3.19 | 96 |
| 6 | 28.8 | 3.26 | 98 |
| 7 | 34.5 | 3.30 | 99 |
| 8 | 40.2 | 3.30 | 99 |
| 9 | 46.0 | 3.33 | 100 |

In this experiment, the methanol was added to the sample reservoir just before measurement #1. As the sample flows through the oxidation reactor and the $CO_2$ sensor, the concentration of total carbon begins to increase and stabilizes to within 98% of the final value after 6 measurements (29 min.), reflecting the "dead" volume of the test apparatus and a "stabilization" time required for the $CO_2$ membrane module. Correcting the TC values for the known recovery of the membrane module, the average value of TC for this test was 3.97 ppm C, or only a 1.6% error.

Tests of the oxidation reactor at higher methanol concentrations using U.V. only (no electrolysis) indicate that the maximum TOC concentration that can be completely oxidized by this technique is about 5–6 ppm C. This upper level, however, still is about two times greater than the maximum concentration of methanol that could be oxidized using a coiled quartz reactor without an inorganic hydrogen-absorbing member.

EXAMPLE VII

A series of tests were then performed to help define the optimum operating conditions of the electrolysis portion of the oxidation reactor. The results from these tests are summarized below.

TABLE VI

INITIAL TEST OF COMBINED ELECTROLYSIS/PHOTOLYSIS
OXIDATION REACTOR FOR THE OXIDATION OF
A 15.0 ppm C METHANOL STANDARD

| | Test Time | I (mA) | V (volts) | TC* (ppm C) |
|---|---|---|---|---|
| 15.0 ppm C (U.V. only) | — | 0 | 0.15 | 4.8–6.6 |
| 15.0 ppm C (Electrolysis and U.V.) | 1 | 2.67 | 1.98 | 12.12 |
| | 2 | 2.14 | 1.98 | 12.45 |
| | 3 | 1.76 | 1.98 | 11.74 |
| | 4 | 1.76 | 1.98 | 10.79 |
| Increase in Applied Potential | | | | |
| | 1 | 3.33 | 2.12 | 10.54 |
| | 2 | 3.65 | 2.11 | 11.38 |
| | 3 | 3.24 | 2.11 | 13.53 |
| | 4 | 3.55 | 2.11 | 13.09 |
| | 5 | 3.29 | 2.11 | 14.00 |
| | 6 | — | 2.11 | 12.81 |
| | 7 | — | 2.11 | 12.45 |
| | 8 | — | 2.11 | 12.10 |
| Further Increase in Applied Potential | | | | |
| | 1 | 3.81 | 2.20 | 15.06 |
| | 2 | 3.38 | 2.20 | 14.65 |

*TOC values corrected for 83.5% recovery of $CO_2$ from the membrane module.

As shown in Table VI, electrolysis-assisted oxidation of methanol was achieved when an electrical potential is applied to the electrolysis cell. For an applied potential of 1.98 V, the maximum conversion efficiency was 83%. As the cell was operated at this electrical potential, the conversion efficiency and cell current both gradually decreased over time between test time (1) and test time (4). Increasing the applied potential to 2.11 V resulted in an initial increase in cell current and conversion efficiency (up to 93%), but again both cell current and conversion efficiency gradually decreased over time between test time (1) and test time (8). In a third test with operation at 2.20 V, substantially complete oxidation of the methanol was initially realized; but, as before, cell current and conversion efficiency decreased over time between test time (1) and test time (2).

In all of the experiments described above, the U.V. lamps were on. In order to determine the oxidation efficiency for electrolysis alone, another test was run wherein the conversion efficiency for a 21 ppm C solution of methanol was determined with the lamps on and off, and the electrolysis cell operated at 1.89 V and a cell current of 14.9 mA. The conversion efficiency with combined electrolysis/photolysis for the solution was found to be in the range of 98–107%. But, conversion efficiency decreased to about 19–21% with the lamps off. Clearly photolysis, or an alternative source of energy to the oxidation cell, is an important factor for the complete oxidation of methanol.

Further experiments suggest the desirability in some cases of operating the apparatus of this invention on a more complex series of alternating absorption/oxidation cycles and cleansing/regeneration cycles. In this more complex operating mode, "normal" operation might comprise, for example, alternating relatively short (e.g., 5–20 seconds) positive-polarity absorption/oxidation cycles with relatively short (e.g., about 1–4 seconds) reverse-polarity cleansing/regeneration cycles. Periodically, either at pre-determined intervals or based on system performance feedback from monitoring oxidation efficiencies, e.g., by monitoring ORP or dissolved oxygen concentration in the samples leaving the reactor, a longer and more thorough reverse-polarity cleansing/regeneration cycle (e.g., for about 10 min. at a suitable voltage) would be substituted for one of the shorter reverse-polarity cycles to effect a more thorough cleansing/regeneration of the hydrogen-absorbing electrode.

It will be apparent to those skilled in the art that other changes and modifications may be made in the above described apparatus and process without departing from the scope of the invention herein, and it is intended that all matter contained in the above description shall be interpreted in an illustrative and not in a limiting sense.

Having described the invention, what we claim is:

1. An apparatus for the measurement of carbon compounds in an aqueous sample, comprising:
   (a) an oxidation reactor for the conversion of organic compounds in an aqueous sample to carbon dioxide, said reactor comprising:
      (i) means for containing said aqueous sample in said reactor for a controlled period of time such that a portion of said sample is in contact with a surface of a hydrogen absorbing member;
      (ii) means for providing energy to said sample while contained in said reactor;
      (iii) means for surface regeneration of said surface of a hydrogen absorbing member to restore said surface for further hydrogen absorption; and
   (b) a carbon dioxide sensor in communication with said oxidation reactor to determine the carbon concentration in the aqueous sample coming from said reactor.

2. An apparatus according to claim 1 wherein said means for providing energy to said sample comprises an ultraviolet light source to irradiate said sample while it is contained in said reactor.

3. An apparatus according to claim 1 further comprising a second electrically-conductive member spaced apart from said hydrogen-absorbing member and separated therefrom by said sample contained in said reactor, and means for electrically connecting said hydrogen-absorbing member and said second electrically-conductive member to a power supply so as to establish an electrical potential across said sample between the two members wherein said means for providing energy to said sample comprises an ultraviolet light source to irradiate said sample while it is contained in said reactor, and also wherein said second electrically-conductive member is located between said ultraviolet light source and said sample and said second electrically-conductive member is able to transmit at least some ultraviolet light.

4. An apparatus according to claim 3, wherein said second electrically-conductive member comprises an electrically conductive screen.

5. An apparatus according to claim 4, wherein the electrically conductive screen includes a mesh selected from the group consisting of titanium, platinum and gold.

6. An apparatus according to claim 1 wherein said means for containing said aqueous sample in said reactor comprises a serpentine channel defined, at least in part, by said surface of a hydrogen-absorbing member.

7. An apparatus for the measurement of carbon compounds in an aqueous sample comprising:
(a) an oxidation reactor for the conversion of organic compounds in aqueous sample to carbon dioxide, said reactor comprising:
  (i) means for containing said aqueous sample in said reactor for a controlled period of time such that at least a portion of said sample is in contact with a surface of a hydrogen absorbing member comprising an electrically conductive material; and
  (ii) means for providing energy to said sample while contained ins said reactor; and
(b) a carbon dioxide sensor in communication with said oxidation reactor to determine the carbon concentration in the aqueous sample coming from said reactor
said apparatus further comprising a second electrically conductive member spaced apart from said hydrogen absorbing member and separated therefrom by said sample contained in said reactor, and
further comprising means for establishing a first electrical potential across the sample whereby said hydrogen absorbing member functions as a cathode and said second electrically conductive member functions as an anode and also for periodically reversing the electrical polarity between said two members to establish a second reverse electrical potential whereby said hydrogen absorbing member functions as an anode relative to said second electrically conductive member.

8. An apparatus according to claim 7 further comprising means to regulate and vary said first electrical potential and said second reverse electrical potential.

9. An apparatus according to claim 7 further comprising timer means to regulate and vary the respective durations of the period of said first electrical potential and the alternating period of said second, reverse electrical potential.

10. An apparatus for converting organic compounds in an aqueous sample to oxides, said apparatus comprising:
(a) a chamber for containing said aqueous sample during the conversion of said compounds into oxides, said chamber comprising at least in part, a hydrogen absorbing member wherein hydrogen is absorbed by or diffuses into said member;
(b) an ultraviolet light source to irradiate said chamber with ultraviolet light; and,
(c) means for periodically flushing said chamber with a cleansing fluid to remove hydrogen from said hydrogen-absorbing member.

11. An apparatus according to claim 10 wherein said hydrogen-absorbing member is selected from the group consisting of the transition metals and alloys thereof.

12. An apparatus according to claim 10 wherein said hydrogen-absorbing member consists of a material selected from the group consisting of palladium, palladium alloys, platinum, platinum alloys, nickel, nickel alloys, titanium and titanium alloys.

13. An apparatus according to claim 10 wherein said hydrogen-absorbing member comprises an electrically-conductive material.

14. An apparatus according to claim 13 further comprising a second electrically-conductive member spaced apart from said hydrogen-absorbing member and separated therefrom by said sample contained in said reactor, and means for electrically connecting said hydrogen-absorbing member and said second electrically-conductive member to a power supply so as to establish an electrical potential across said sample between the two members.

15. An apparatus according to claim 10, wherein said ultraviolet light source produces at least some light having a wavelength less than 254 nm.

16. An apparatus according to claim 15, wherein the ultraviolet light source is chosen from the group consisting of mercury vapor lamps, xenon-doped mercury lamps, krypton chloride excimer lamps and xenon excimer lamps.

17. An apparatus for converting organic compounds in an aqueous sample to their respective oxides, said apparatus comprising:
(a) a chamber for containing said aqueous sample during the conversion of said organic compounds into their respective oxides, said chamber comprising at least in part an inorganic, hydrogen absorbing, electrically-conductive member wherein hydrogen is absorbed by or diffuses into said member;
(b) an ultraviolet light source to irradiate said chamber with ultraviolet light;
(c) an electrolysis cell comprising a second electrically-conductive member, spaced apart from said hydrogen-absorbing member and positioned between the sample in the chamber and the ultraviolet light source, said second electrically-conductive member being able to transmit at least some ultraviolet light; and,
(d) means for electrically connecting said hydrogen absorbing member and said second electrically-conductive member to a power supply so as to establish a first electrical potential across said chamber between said hydrogen absorbing member and said second electrically-conductive member, whereby said hydrogen absorbing member functions as a cathode and said second electrically-conductive member functions as an anode, and also for periodically reversing the electrical polarity between said two members to establish a second, reverse electrical potential, whereby said hydrogen absorbing member functions as an anode relative to said second electrically-conductive member.

18. A reactor comprising:
(a) a chamber defining a liquid flow path extending from an input port to an output port, said chamber including an electrically-conductive, hydrogen-absorbing sheet member defining a lateral boundary of said flow path, and wherein said chamber includes second electrically-conductive element at or adjacent to a lateral boundary of said flow path opposite to said sheet member, said second element being electrically isolated from said sheet member and able to transmit at least some ultraviolet light;

(b) means for coupling a power source between said second element and said sheet member for establishing said second element as an anode relative to said sheet member;

(c) means for alternately coupling said power source between said sheet member and second element for establishing said second element as a cathode relative to said sheet member; and (d) an ultraviolet light source positioned outside said chamber and adjacent to said second element whereby ultraviolet light is coupled into said chamber.

19. A reactor apparatus for substantially completely converting the organic compounds in a portion of an aqueous sample to carbon dioxide, said apparatus comprising:

(a) an electrolysis cell comprising a first electrode, a second electrode, and a liquid flow path for flowing a substantial portion therebetween;

(b) an ultraviolet light source to irradiate said electrolysis cell with ultraviolet light to promote the conversion of organic compounds to carbon dioxide, further wherein one of said first and second electrodes is located between said ultraviolet light source and said aqueous sample in said electrolysis cell and is able to transmit at least some ultraviolet light and the other of said electrodes comprises an inorganic, hydrogen-absorbing material; and, (c) means for electrically connecting said first and second electrodes to a power supply so as to alternately establish a first electrical potential across said electrolysis cell whereby said hydrogen-absorbing electrode functions as a cathode, or so as to establish a second electrical potential across said electrolysis cell whereby said hydrogen-absorbing electrode functions as an anode.

20. The apparatus of claim 19 further comprising monitoring means for monitoring the oxidation potential in an aqueous sample leaving the reactor.

21. The apparatus of claim 19 further comprising control means for controlling the respective durations of said alternating first and second electrical potentials.

* * * * *